United States Patent [19]

Bardy

[11] Patent Number: 5,334,221
[45] Date of Patent: Aug. 2, 1994

[54] METHOD AND APPARATUS FOR TREATMENT OF ANGINA SAME

[75] Inventor: Gust H. Bardy, Seattle, Wash.
[73] Assignee: Medtronic, Inc., Minneapolis, Minn.
[21] Appl. No.: 86,278
[22] Filed: Jun. 30, 1993

Related U.S. Application Data

[63] Continuation of Ser. No. 906,959, Jun. 30, 1992, abandoned.

[51] Int. Cl.$^5$ ............................................. A61N 1/362
[52] U.S. Cl. ................................................. 607/14
[58] Field of Search ........................... 607/4, 5, 6, 9, 14

[56] References Cited

U.S. PATENT DOCUMENTS

| | | | |
|---|---|---|---|
| 3,878,564 | 4/1975 | Yao et al. | 128/419 B |
| 4,485,813 | 12/1984 | Anderson et al. | 128/675 |
| 4,535,774 | 8/1985 | Olson | 128/419 |
| 4,686,988 | 8/1987 | Sholder | 128/419 PT |
| 4,750,495 | 6/1988 | Moore et al. | 128/419 PG |
| 4,880,005 | 11/1989 | Pless | 128/419 PG |
| 4,998,974 | 3/1991 | Aker | 128/419 PG |
| 5,203,326 | 4/1993 | Collins | 607/4 |
| 5,243,980 | 9/1993 | Mehra | 607/6 |

OTHER PUBLICATIONS

Application Serial No. 07/736,198 by Bennett et al., filed Jul. 26, 1991.
Application Serial No. 07/673,883 by Obel et al., filed Mar. 22, 1991.
Article "Special Considerations" in Cardiac Pacemakers by Harold Siddons et al., pp. 200–217, Charles C. Thomas Publisher.
Bilgutay et al., "Vagal Tuning", Journal of Thoracic and Cardiovascular Surgery, vol. 56, Jul. 1968, pp. 71–82.
Bluemel et al., "Parasympathetic Postganglionic Pathways to the Sinoatrial Node", American Journal of Physiology, 259: H1504–H1510, 1990.
Braunwald, et al., "Carotid Sinus Nerve Stimulation in the Treatment of Angina Pectoris and Supraventricular Tachycardia", California Medicine, 112:41–50, Mar. 1970.
Cooper et al, "Neural Effects on Sinus Rate and Atrioventricular Conduction Produced by Electrical Stimulation from a Transvenous Electrode Catheter in the Canine Right Pulmonary Artery", Circulation Research, vol. 46, No. 1, Jan. 1980, pp. 48–57.
Randall et al, "Functional Anatomy of the Cardiac Efferent Innervation", Neurocardiology, Mount Kisco, N.Y., Futura Publishing Co, Inc. 1988, pp. 3–24.

Primary Examiner—William E. Kamm
Assistant Examiner—George Manuel
Attorney, Agent, or Firm—Reed A. Duthler; Harold R. Patton

[57] ABSTRACT

A stimulator for providing stimulus pulses to the SA nodal fat pad, in response to heart rate exceeding a predetermined level, in order to reduce the ventricular rate. The device is also provided with a cardiac pacemaker to pace the ventricle in the event that the stimulus pulses reduce the heart rate below a predetermined value. The device is also provided with a feedback regulation mechanism for controlling the parameters of the stimulation pulses applied to the AV nodal fat pad, as a result of their determined effect on heart rate.

20 Claims, 7 Drawing Sheets

METHOD AND APPARATUS FOR TREATMENT OF ANGINA SAME

This is a continuation of copending application Ser. No. 07/906,959 filed on Jun. 30, 1992, now abandoned.

BACKGROUND OF THE INVENTION

This invention relates to implantable stimulators generally and more particularly to implantable nerve stimulators and pacemakers.

It is known that stimulation of the vagus nerve can reduce the sinus rate, as well as prolong the AV conduction time or, if stimulation energies are high enough, induce A-V block. Use of vagal nerve stimulation to treat supraventricular arrhythmias and angina pectoris is disclosed in the article "Vagal Tuning" by Bilgutay et al., *Journal of Thoracic and Cardiovascular Surgery*, Vol. 56, No. 1, July, 1968, pp. 71-82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in *California Medicine*, Vol. 112, pp. 41-50, March, 1970.

The nervous system regulating the rhythm of the heart also includes a number of highly ganglionated plexi or "fat pads" at various locations on the heart, including fat pads associated with the SA and AV nodes. The fat pad associated with the SA node is located overlying the right pulmonary vein entrance in dogs, and is located along the anterior AV groove in most humans. The fat pad associated with the AV node is located at the junction of the inferior vena cava and the inferior left atrium in dogs, and is located along the posterior AV groove in most humans.

As set forth in "Functional Anatomy of the Cardiac Efferent Innerration" by Randall et al, in *Neurocardiology*, edited by Kulbertus etal, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node", Bluemel et al, Am. J. Physiol. 259, (Heart Circ. Physiol. 28) H1504-H1510, 1990, stimulation of the fat pad associated with the SA node results in slowing of the sinus rate without the accompanying prolongation of A-V conduction time which normally results from vagal nerve stimulation. The article also indicates that stimulation of the fat pad associated with the AV node is believed to produce corresponding effects limited to the AV node, i.e. extension of the A-V conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48-57, the fat pads associated with both the AV node and the SA node may be stimulated by means of electrodes located in the right pulmonary artery. The results obtained include both a depression of the sinus rate and a prolongation of the A-V conduction time in response to continuous stimulation at 2-80 Hz at up to 50 ma.

SUMMARY OF THE INVENTION

It has been determined by Rahul Thehra that continuous fat pad stimulation of the sort set forth in the Cooper et al. article often leads to induction of atrial fibrillation. However, by providing only limited bursts of stimulation, synchronized to detected atrial depolarizations, the problem of atrial fibrillation induction can be avoided. Moveover, the desired result of slowing the sinus rate, can still be accomplished. These factors allow the use of electrical stimulation of the SA nodal fat pad to provide a practical method for treatment of angina pectoris.

The device embodying the present invention includes means for measuring physiologic parameters indicative of the occurrence of angina. The parameter or parameters measured may be the atrial rate alone or may be the atrial rate in conjunction with one or more additional parameters such as venous oxygen saturation, cardiac blood pressure, systemic blood pressure, or cardiac output. Following detection of conditions indicative of angina, the device responds by stimulating the SA nodal fat pad synchronized to detected atrial depolarizations. Stimulation may be accomplished by means of a lead carrying electrodes located in the right atrium and/or coronary sinus. Alternatively, fat pad stimulation may be accomplished by means of epicardial or myocardial electrodes applied directly to the SA nodal fat pad.

Stimulation of the SA nodal fat pad results in a reduction in the sinus rate. The invention therefore also includes a pacemaker to assure that the effects of fat pad stimulation do not result in an inadequate heart rate. The atrial rate threshold and any other required measured parameter values for initiation of fat pad stimulation are preferably specified by the physician based on the condition of the patient in whom the device is to be implanted. The amplitude of the burst stimulus pulses is selected to produce a slowing of the sinus rhythm to a rate below the rate threshold for initiation of fat pad stimulation, but preferably above a second, intermediate rate, which in turn is above the base pacing rate of the pacemaker. Adjustment of the stimulus pulse amplitude may be performed by the physician but is preferably performed automatically by the implanted stimulator, based upon the sensed change in sinus rhythm following delivery of burst stimulation.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENTS

FIGS. 1A through 1E are simulated atrial electrograms and timing diagrams illustrating the operation of a device embodying the present invention. Generally, the present invention provides a burst of one or more pulses intended to stimulate the sinus node, delivered synchronized to sensed atrial depolarizations. The pulse bursts are not intended to induce depolarization of the atrium, and therefore are delivered during the atrial refractory period, immediately following the occurrence of sensed atrial depolarizations.

The device is designed such that in following the detection of an atrial rate above a first rate, hereinafter referred to as the "upper rate", the device delivers the synchronized bursts discussed above. The burst stimulation is delivered in an effort to reduce the atrial rate to a rate less than the upper rate, but greater than a second rate, hereinafter referred to as the "intermediate rate". In the event that the atrial rate falls below and remains below the intermediate rate, synchronized burst stimulation ceases.

As noted above, verification of the occurrence of angina by means of a second measured parameter may also be required as a prerequisite to initiation of burst stimulation. In such an embodiment, the burst stimulation may also be terminated in response to the second measured parameter exceeding or falling below a predetermined threshold, even without the atrial rate falling persistently below the intermediate rate.

The amplitude of the burst stimulation is adjusted automatically, such that the atrial rate during burst stimulation is reduced to a rate below the upper rate, but greater than the intermediate rate. Adjustment of the stimulus pulse amplitude is accomplished by measuring the P—P interval following burst stimulation, and using this measured value to regulate the stimulation pulse amplitude. If the measured P—P interval following delivery of a synchronized burst is less than a first interval corresponding to the upper rate, the burst amplitude for the next burst is increased. This first interval is referred to hereafter as the "upper rate interval". If the P—P interval following burst stimulation is greater than a second interval (intermediate rate interval) corresponding to the intermediate rate, the amplitude of subsequent stimulation bursts is reduced.

In this fashion, a self-regulating system is provided which allows for reduction of the sinus rate, without the risk of prolonged excessively depressed sinus rates in the presence of exercise. The values of the upper rate and the intermediate rates, as well as any additional measured parameter threshold values are preferably selected by the physician, and tailored to the requirements of the individual patient in whom the device is implanted.

In addition to defining the criteria for decrementing the burst stimulus pulse amplitude, the intermediate rate interval also defines the longest P—P interval following which synchronized burst stimulation will be delivered. That is, synchronized burst stimulation will only be delivered synchronized to P waves which define the end point of P—P intervals less than the intermediate rate interval.

Preferably, the criteria for activating and deactivating the burst stimulus function exhibit a significant degree of hysteresis. For example, a predetermined number of successive P-waves at or above the upper rate will typically be required in order to activate the burst stimulation function. Typically, a second predetermined number of P-waves at a rate lower than the intermediate rate will be required in order to disable the burst stimulation function. Once the burst stimulation function has been enabled, bursts will be delivered depending upon a preset therapy schedule and depending upon the sensed duration of P—P intervals following burst stimulation. As discussed above, in the event that a P—P interval exceeds the intermediate rate interval, no burst stimulation pulses will be delivered, even if the burst stimulation function has been activated.

Similarly, in the event a second measured parameter is employed for initiation of the burst stimulation function, it is expected that the threshold value for disabling the burst stimulation function will different from the threshold value for initiation. For example, if a reduction of mixed venous oxygen saturation below a first value is required in order to initiate burst pacing, an increase in oxygen saturation to a second value above the first value would be required to terminate burst stimulation.

In addition, it is anticipated that in some cases, burst stimulation may not be required following each sensed P-wave, even if the sensed P-wave does define a P—P interval less than the intermediate rate interval. For example, if the intrinsic atrial rate is only slightly above the upper rate, stimulation may be delivered synchronized one of every two or one of every three sensed P-waves occurring at a rate above the upper rate. On the other hand, if the sensed natural atrial rate is substantially in excess of the upper rate, burst stimulus pulses may be delivered synchronized to each sensed P-wave in order to avoid an excessively irregular heart rhythm.

FIGS. 1A through 1E illustrate the operation of the device as discussed above. In each of these figures, the upper strip is a simulated atrial electrogram and the lower tracing is a simulated timing diagram illustrating the timing and amplitude of synchronized stimulation pulses. For the sake of simplicity, ventricular contractions are not illustrated. However, it is to be understood that in patients with intact conduction systems, ventricular contractions are expected to follow the sensed atrial contractions. In patients in which the invention is embodied in a dual chamber (DDD) pacemaker, ventricular pacing pulses and stimulated ventricular depolarizations may also follow the sensed atrial depolarizations, if the patient's intrinsic AV interval is greater than the pacemaker's defined AV interval or if natural AV conduction is lacking.

Figure 1A:
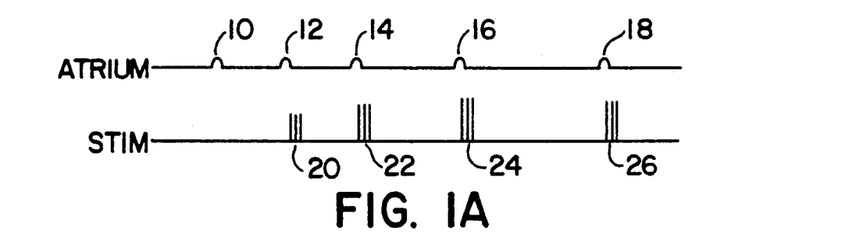
FIGS. 1A–1E include simulated atrial EGM tracings and timing diagrams, illustrating the basic operation of the present invention.

FIG. 1A illustrates the basic operation of the device on sensing the occurrence of a rapid atrial rhythm. In this case, the device is programmed such that after detection of a rapid atrial rhythm has occurred, burst stimulus pulses will be delivered synchronized to each detected P wave occurring at a rate in excess of the intermediate rate.

Simulated P waves 10 and 12 indicate the occurrence of an atrial rate above the upper rate. After the occurrence of a predetermined number of such high rate P-waves, the burst stimulation function is activated, and a burst of pulses 20 is delivered synchronized to detected P wave 12. Pulses are illustrated as initially presented at a relatively low amplitude. As illustrated by the timing of P-wave 14, pulse 20 was not effective in reducing the sinus rate. Therefore, the next burst of pulses 22 is provided at an increased amplitude, synchronized to depolarization 14. Burst 22 results in a prolongation of the P—P interval as indicated by the extended P—P interval between p waves 14 and 16. However, in the case illustrated, the interval between P waves 14 and 16 still less than the upper rate interval. Therefore, the third burst of synchronized pulses 24 is delivered at a second increased amplitude.

This second increase in pulse amplitude results in a further reduction in sinus rate, as indicated by the prolongation of the interval separating P-waves 16 and 18. Because the interval separating P-waves 16 and 18 is greater than the upper rate interval, the stimulation pulse amplitude is considered to be adequate, and the next synchronized burst at 26 is delivered at the same pulse amplitude. Thus, the device automatically adapts its stimulation pulse energy to the minimum value necessary to decrease the sinus rate to a level below the preset upper rate.

Figure 1B:
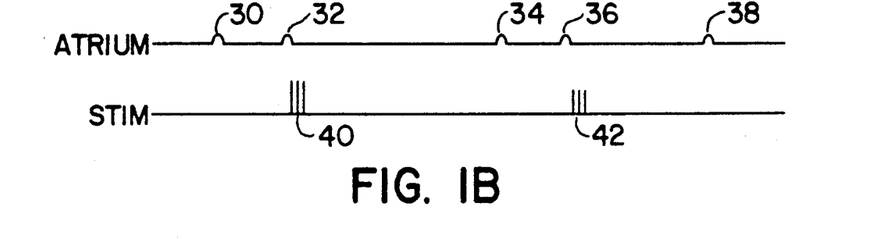

FIG. 1B illustrates the situation in which the initial amplitude of the stimulation pulses produces an excessive slowing of the heart rate. P waves 30 and 32 again reflect a natural heart rate substantially in excess of the physician defined upper rate, resulting in activation of the burst stimulation feature. At 40, a burst of stimulation pulses is delivered synchronized to detected P wave 32. The resultant slowing of the atrial rate is substantial, such that no spontaneous P wave occurs prior to expiration of the pacemaker's escape interval. Therefore, an atrial pacing pulse is delivered at 34, causing an evoked atrial contraction. Because the interval separating P wave 32 from paced P wave 34 exceeds the intermediate rate interval, no burst stimulus pulses are provided and the amplitude of the stimulus pulses for the next burst is decremented. Thus, on occurrence of the next spontaneous P-wave 36 at a rate above the upper rate, a reduced amplitude pulse burst is delivered at 42. This pulse burst is also effective in slowing the atrial rate, however, as indicated by the timing of P wave 38, the resultant P-P interval is less than the intermediate rate interval, and the pulse amplitude is thus indicated to be acceptable.

Figure 1C:
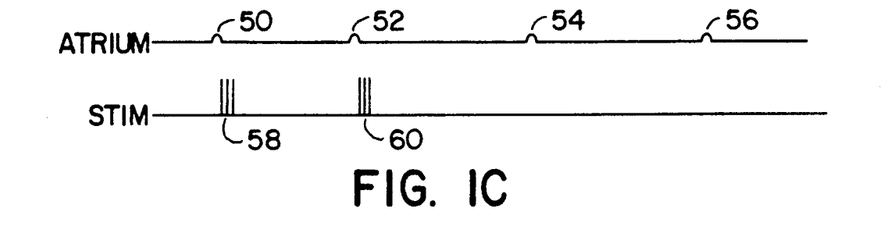

FIG. 1C illustrates the mechanism by which the burst stimulation mode is exited, on normal decrease of atrial rhythm. As illustrated, the burst stimulation function has been activated previously, as illustrated by stimulus pulse bursts 58 and 60 synchronized to P-waves 50 and 52. P-wave 54 follows P-wave 52 by an interval greater than the intermediate rate interval such that no synchronized stimulation burst is provided. P-wave 56 also follows P-wave 54 by an interval greater than the intermediate rate interval. Because the interval separating P-waves 54 and 56 reflects the atrium's intrinsic rhythm, and because that rhythm is below the intermediate rate, the device determines that burst stimulation is no longer required. The burst stimulation function is therefore disabled.

Disabling of the burst stimulation function can be accomplished in response to the occurrence of a predetermined number (one or more) of sequential P—P intervals greater than the intermediate rate interval in which the P-waves initiating the intervals were not accompanied by stimulus bursts. Requiring the occurrence of such intervals as a criteria for disabling the burst stimulation function prevents turn off of the burst stimulation function in situations in which an excessive stimulation pulse amplitude has produced a misleadingly great prolongation of the P—P interval.

As discussed above, if a second measured parameter is employed, disabling of the burst stimulation function may also occur in response to a second measured parameter falling below or rising above a predetermined threshold, even if the atrial rate does not persistently remain below the intermediate rate.

Figure 1D:
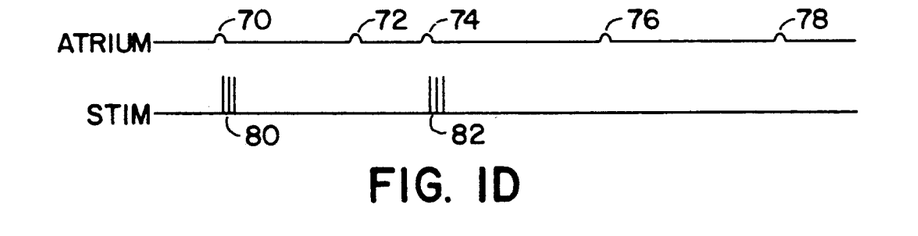
Figure 1E:
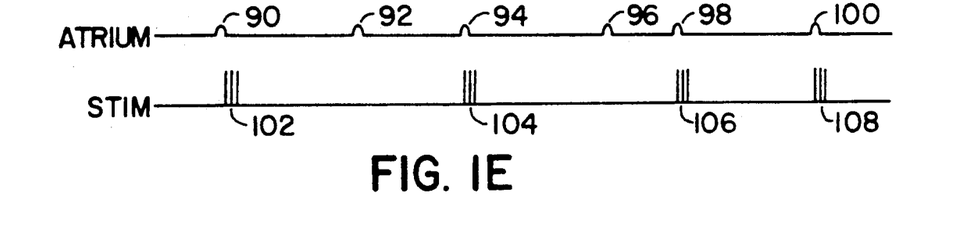

FIGS. 1D and 1E illustrate the operation of embodiments of the device in which different therapy schedules are provided, depending upon the detected rate of spontaneous atrial depolarizations. In a device as illustrated in FIGS. 1D and 1E, in the presence of a natural atrial rate exceeding the upper rate by only a moderate amount, stimulus bursts are only delivered to one out of every two P-waves occurring at a rate above the intermediate rate, rather than synchronized to every such P-wave. Because the prolonged P—P intervals resulting from stimulation will not be too much greater than the natural escape intervals, it is believed that this degree of irregularity in heart rhythm can be tolerated by the patient without undue consequences. By cutting the number of stimulus bursts in half, in this circumstance, a substantial prolongation of battery life may be accomplished. On the other hand, in the event that the patient's intrinsic atrial rate is substantially above the upper rate, after activation of the burst stimulation feature, every P-wave occurring at a rate above the intermediate rate results in synchronized stimulation, to provide a more even heart rhythm.

FIG. 1D illustrates the circumstance in which the sensed atrial rate is only slightly above the prescribed upper rate. A first stimulation burst 80 is delivered synchronized to P-wave 70. The next P-wave 72, although it defines the endpoint of a P—P interval less than the intermediate rate interval, does not result in delivery of a synchronized pulse burst. The next P wave 74, occurring after an interval less than the intermediate rate interval, does elicit a synchronized pulse burst at 82. P-waves 76 and 78 both terminate P—P intervals corresponding to a rate less than the intermediate rate, and thus result in turn off of the burst stimulation feature.

FIG. 1E illustrates a situation in which acceleration of the patient's natural atrial rate results in an increase in the burst stimulation therapy schedule. As illustrated, pulse burst 102 is delivered synchronized to atrial contraction 90. In this case, it is assumed that the sensed spontaneous atrial rate is presently only slightly above the upper rate, as illustrated by the P—P interval separating P-waves 92 and 94. Therefore, stimulus bursts are only provided synchronized to every other detected P-wave, as illustrated by the synchronous pulse burst provided at 104. No pulse burst is provided synchronized to P-wave 96.

However, P-wave 98 follows P-wave 96 by an interval sufficiently short to indicate a rate substantially in excess of the upper rate. The device recognizes this fact, and accelerates the therapy schedule such that synchronized stimulation bursts are thereafter provided with each detected P-wave occurring at a rate above the intermediate rate, in order to avoid an excessively irregular rhythm. This function is illustrated by pulse bursts 106 and 108 synchronized to P-waves 98 and 100.

As such, a device embodying the present invention will provide automatic adjustment of amplitude and/or burst therapy regimen in response to the detected effect of the stimulation on the P—P interval and in response to changes in the patient's intrinsic atrial rhythm, respectively. The device embodying the present invention also automatically deactivates the burst stimulus pulse therapy, where appropriate, and provides back up atrial and optionally ventricular pacing as a safety feature in the event that the burst stimulation pulses results in an excessive reduction in the sinus rhythm.

Figure 2:
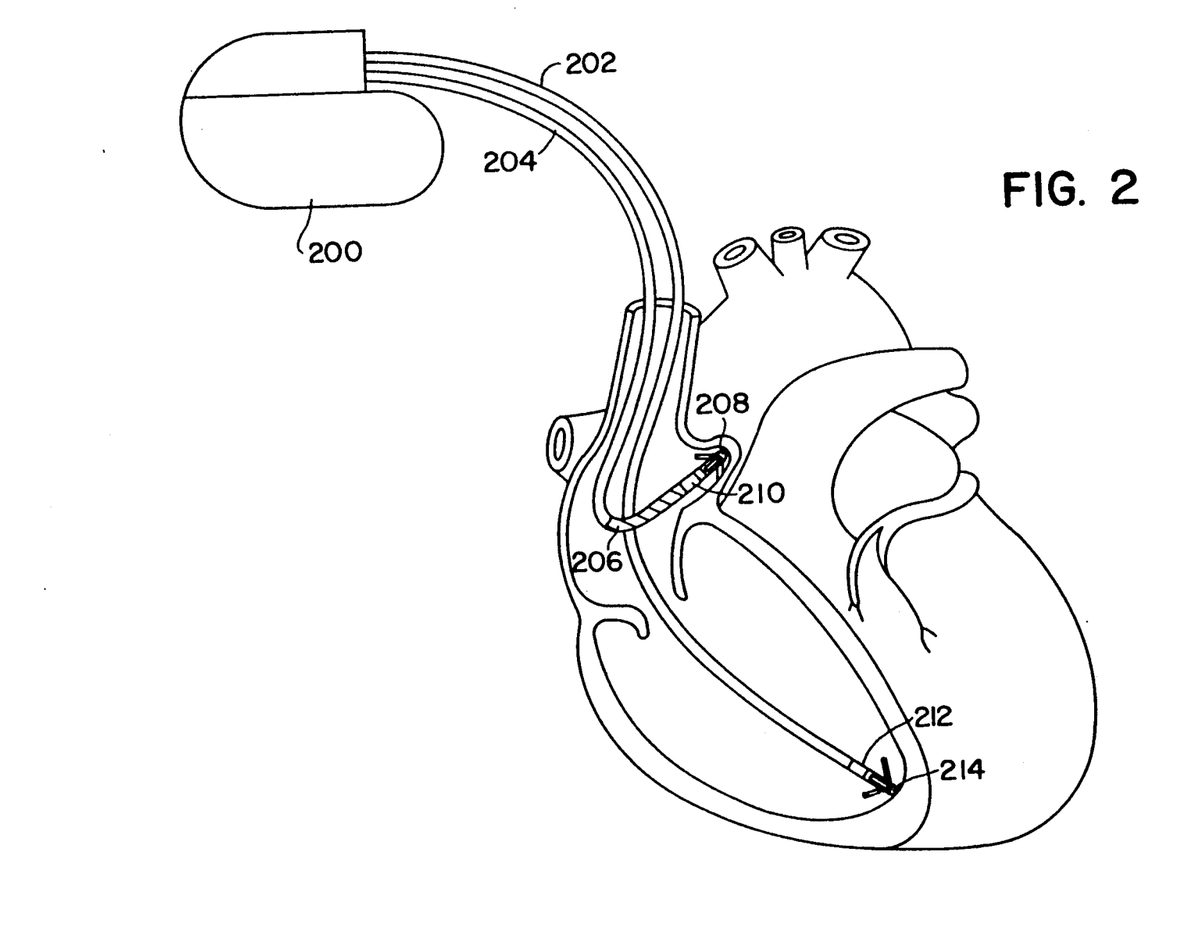
FIG. 2 is an illustration of one embodiment of a combination pacing and fat pad stimulation lead system for use with the present invention.

FIG. 2 is a cutaway view of the heart illustrating an implantable pacemaker/fat pad stimulator and an associated lead system. The combination pacemaker/fat pad stimulator 200 is shown diagrammatically, and is provided with two endocardial leads 202 and 204 which enter the heart through the superior vena cava. Lead 204 is an atrial lead having a J-shaped configuration adapted to locate its distal end in the right atrial appendage, similar to atrial pacing leads presently marketed. Lead 204 is provided with a closely spaced pair of electrodes 208 and 210 which function to sense spontaneous atrial depolarizations and to pace the atrium, if necessary. An elongated coil electrode 206 is provided, adapted to lay along the anterior of the atrium, positioned generally adjacent to the anterior A-V groove, to stimulate the SA nodal fat pad. Stimulation of the SA nodal fat pad may be accomplished by delivery of pulses between electrode 206 and the case of the stimulator 200 or between electrode 206 and electrodes 208 and 210. In the embodiment illustrated, the combined pacemaker/fat pad stimulator takes the form of a dual chamber pacemaker, and is thus provided with a ventricular lead 202, provided with two electrodes 212 and 214 adapted for location in the right ventricular apex.

While the lead system illustrated is based on the presumption that the SA nodal fat pad will lie along the anterior AV groove, the variation of heart anatomy from patient to patient may be substantial. Therefore, in some cases, it may be desirable to stimulate the SA nodal fat pad by means of an electrode located in the proximal coronary sinus, in cases in which the fat pad associated with the sinus node is located more closely to the posterior AV groove. Similarly, in other cases it may be more desirable to directly stimulate the fat pad associated with the SA node by means of epicardial or myocardial electrodes applied directly to, embedded in, or located adjacent to the fat pad.

Figure 3:
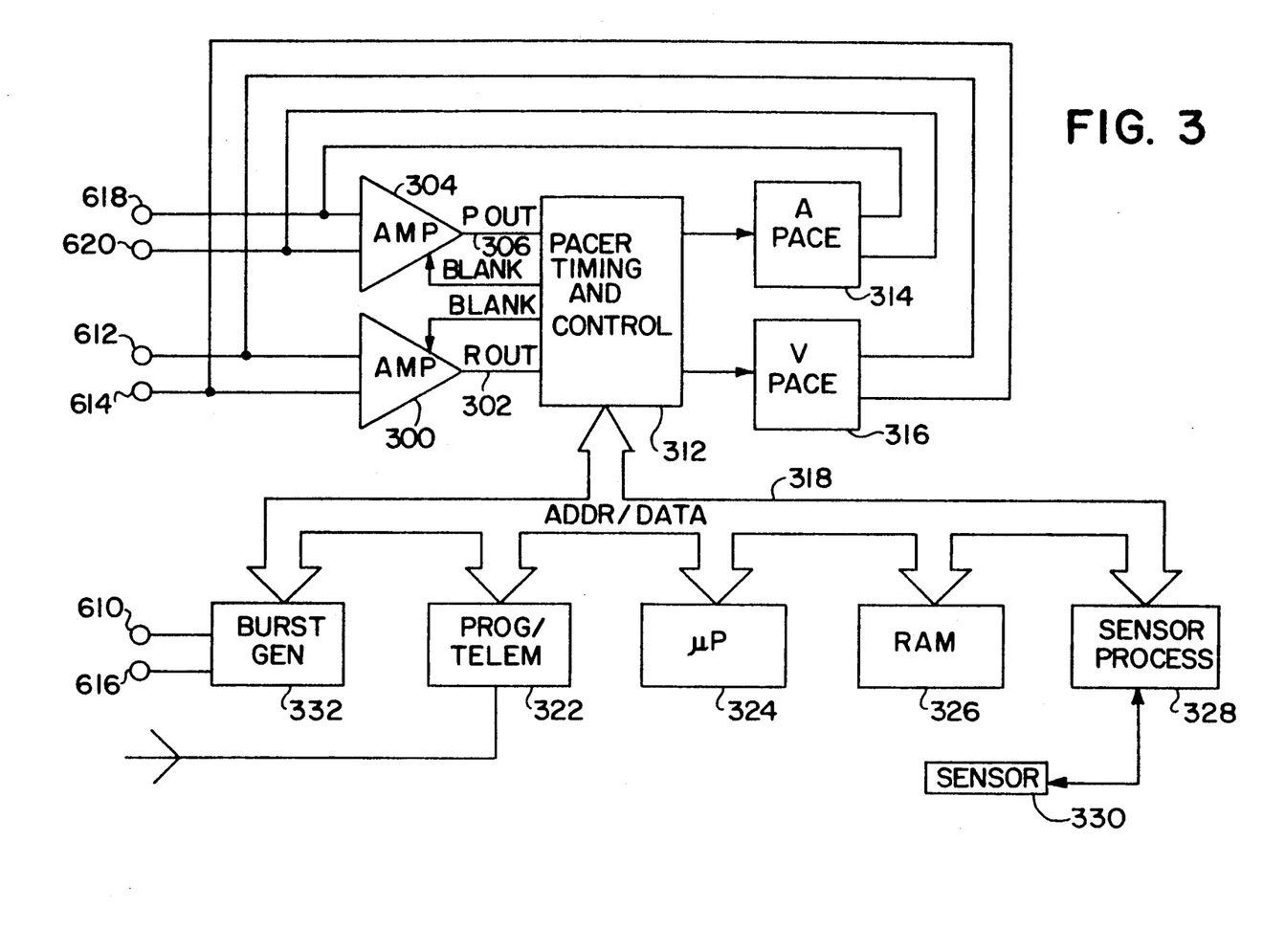
FIG. 3 is a functional block diagram illustrating an implantable pacemaker/fat pad stimulator in which the present invention may be embodied.

FIG. 3 is a functional schematic diagram of an implantable pacemaker/fat pad stimulator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemakers and/or pacemaker/cardioverter/defibrillator presently commercially sold or being implanted for clinical evaluation in the United States.

The device is provided with an electrode system including electrodes as illustrated in FIG. 2. Electrode 616 corresponds to electrode 206, FIG. 2. An additional electrode 610 may be an indifferent electrode located on the housing of the implantable pacemaker/fat pad stimulator. As discussed, other electrode configurations for SA nodal fat pad stimulation may also be used.

Electrodes 612 and 614 are located on or in the ventricle and are coupled to the R-wave amplifier 300, which preferably takes the form of a gain controlled amplifier providing an adjustable sensing threshold as a function of the measured R-wave amplitude. A signal is generated on R-out line 302 whenever the signal sensed between electrodes 612 and 614 exceeds the present sensing threshold.

Electrodes 618 and 620 are located on or in the atrium and are coupled to the P-wave amplifier 304, which preferably also takes the form of a gain controlled amplifier providing an adjustable sensing threshold. A signal is generated on P-out line 306 whenever the signal sensed between electrodes 618 and 620 exceeds the present sensing threshold.

The band pass characteristics of amplifiers 200 and 204 may be optimized for sensing R-waves and P-waves, respectively. The general operation of the R-wave and P-wave amplifiers 300 and 304 may correspond to any of the numerous such amplifiers presently employed in cardiac pacemakers.

Burst generator 332 may employ any appropriate technology for generation of stimulation pulses in the form of individual pulses or pulse trains, having amplitudes up to 30 ma, pulse widths of up to 2 ms, and frequencies of up to 1000 Hz. For example, the Medtronic Model 2349 Programmable Stimulator, as discussed in the above cited Cooper et al reference includes circuitry for generating appropriate stimulation pulses and trains. Given that circuitry for pulse generation has become well known to those skilled in the art, no detailed disclosure is included herein. The specific timing, amplitude, duration and number of pulses is controlled by microprocessor 324 via address/data bus 318 under control of the programming stored in random access memory 326. Programming of the device is accomplished by means of telemetry circuit 322, which may correspond to circuitry employed to accomplish this function in prior art pacemakers.

Much of the remainder of the circuitry is dedicated to the provision of cardiac pacing therapies, which for purposes of the present invention may correspond to the prior art. The pacer timing/control circuitry 312 includes programmable digital counters which control the basic time intervals associated with DDD, VVI, DVI, VDD, AAI, DDI or other modes of single and dual chamber pacing well known to the art. Circuitry 312 also may optionally also control escape intervals associated with antitachyarrhythmia pacing in both the atrium and the ventricle, employing any tachyarrhythmia detection and pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 324, in response to stored data in memory 326 and are communicated to the pacing circuitry 312 via address/data bus 318. Pacer circuitry 312 also determines the amplitude of the cardiac pacing pulses under control of microprocessor 324.

During pacing, the escape interval counters within pacer timing/control circuitry 312 are reset upon sensing of R-waves and P-waves as indicated by signals on lines 302 and 306, and in accordance with the selected mode of pacing, on timeout trigger generation of pacing pulses by pacer output circuitry 314 and 316, which are coupled to electrodes 118, 120, 112, 114. The escape interval counters are also reset on generation of pacing pulses, and thereby control the basic timing of cardiac pacing functions, including antitachyarrhythmia pacing. The durations of the intervals defined by the escape interval timers are determined by microprocessor 324, via data/address bus 318. The values of the counts present in the escape interval counters when reset by sensed R-waves and P-waves may also be used to measure the durations of R—R intervals, P—P intervals, P-R intervals and R-P intervals.

Microprocessor 324 operates as an interrupt driven device, and is awakened by interrupts from pacer timing/control circuitry 312 corresponding to the occurrence sensed P-waves and R-waves and corresponding to the generation of cardiac pacing pulses. These interrupts are provided via data/address bus 318. Any necessary mathematical calculations to be performed by microprocessor 324 and any updating of the values or intervals controlled by pacer timing/control circuitry 312 take place following such interrupts.

For example, in response to a sensed or paced ventricular depolarization or R-wave, the intervals separating that R-wave from the immediately preceding R-wave, paced or sensed (R—R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced or sensed atrial contraction (P—P interval) and the interval separating the sensed P-wave from the immediately preceding sensed or paced ventricular depolarization (R—P interval) may be stored.

In response to an analysis of the stored P—P intervals, microprocessor 324 detects whether or not the intrinsic atrial rate meets the predetermined criteria for activation of the burst stimulation function. In the event that these criteria are met, microprocessor 324 triggers burst generator 332 to deliver stimulation pulses synchronized to detected atrial depolarizations or P waves. These pulses are preferably delivered during the refractory period of the atrium, as discussed above, and therefore are typically delivered after a delay of 10-50 milliseconds following sensing of the atrial depolarization by amplifier 304. Operation of the microprocessor to control the pacer circuitry 312 and the burst generator 322, both in single chamber (AAI) and dual chamber (DDD) pacing modes is described in conjunction with the flow charts illustrated in FIG. 4A through 4D.

Optionally the device may include a sensor 330 and associated sensor processing circuitry 328, which presents digitized sensor derived values of a physiologic parameter to microprocessor 324. Sensor 330 may be an oxygen sensor, as disclosed in U.S. Pat. No. 4,750,495 issued to Moore et al on Jul. 31, 1989, incorporated herein by reference in its entirety. In such case, sensor 330 would preferably be located in the right ventricle, right atrium or coronary sinus of the heart. Sensor 330 may alternately be a pressure transducer as disclosed in U.S. Pat. No. 4,485,813 issued to Anderson et al on Dec. 4, 1984, also incorporated herein by reference in its entirety. In such case, sensor 330 may similarly be located in the right ventricle of the heart. Sensor 330 may instead be a ventricular impedance plethysmograph as disclosed in U.S. Pat. No. 4,535,774 issued to Olson on Aug. 20, 1985, also incorporated herein by reference in its entirety.

In the event that a physiologic sensor is employed, the output of the sensor is compared to predetermined thresholds by microprocessor 324 in conjunction with activation and deactivation of the burst stimulation function. In order to activate the burst stimulation function, the sensor threshold is defined so as to be indicative of a cardiac output which is below a desired level, in the context of an atrial rate above the upper rate as discussed above. For example, venous oxygen saturation or stroke volume of less than first predetermined values, in conjunction with an atrial rate of greater than the upper rate may activate burst stimulation. An increase in oxygen saturation or stroke volume above second predetermined values above the first values may trigger termination of burst stimulation, as an alternative to detection of atrial rate persistently below the intermediate rate.

For purposes of initiating and terminating burst pacing, the sensor values to be compared to the defined thresholds are average values, taken over the preceding time intervals. The time interval over which the average values are calculated may be quite short prior to initiation of burst stimulation, for example on the order of a few seconds, to allow rapid response to the onset of angina. in any case, it is preferable that the time period not be in excess of that required to meet the atrial rate criterion for initiation. The time period over which sensor values are averaged may be substantially increased following initiation of burst stimulation, so that a momentary change in sensor output does not inappropriately terminate burst stimulation. Specific time intervals for sensor averaging purposes are determined by the physician and programmed externally, depending on the particular sensors used and the condition of the patient.

Figure 4A:
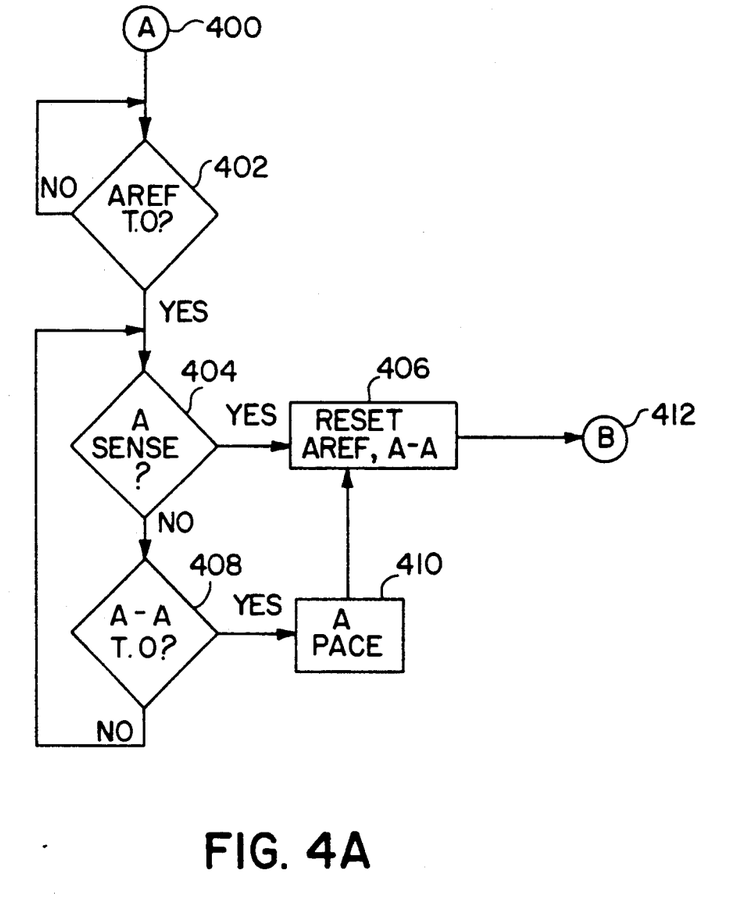
FIGS. 4A–4D are functional flow charts illustrating methods of operation of the device illustrated in FIG. 3.
Figure 4B:
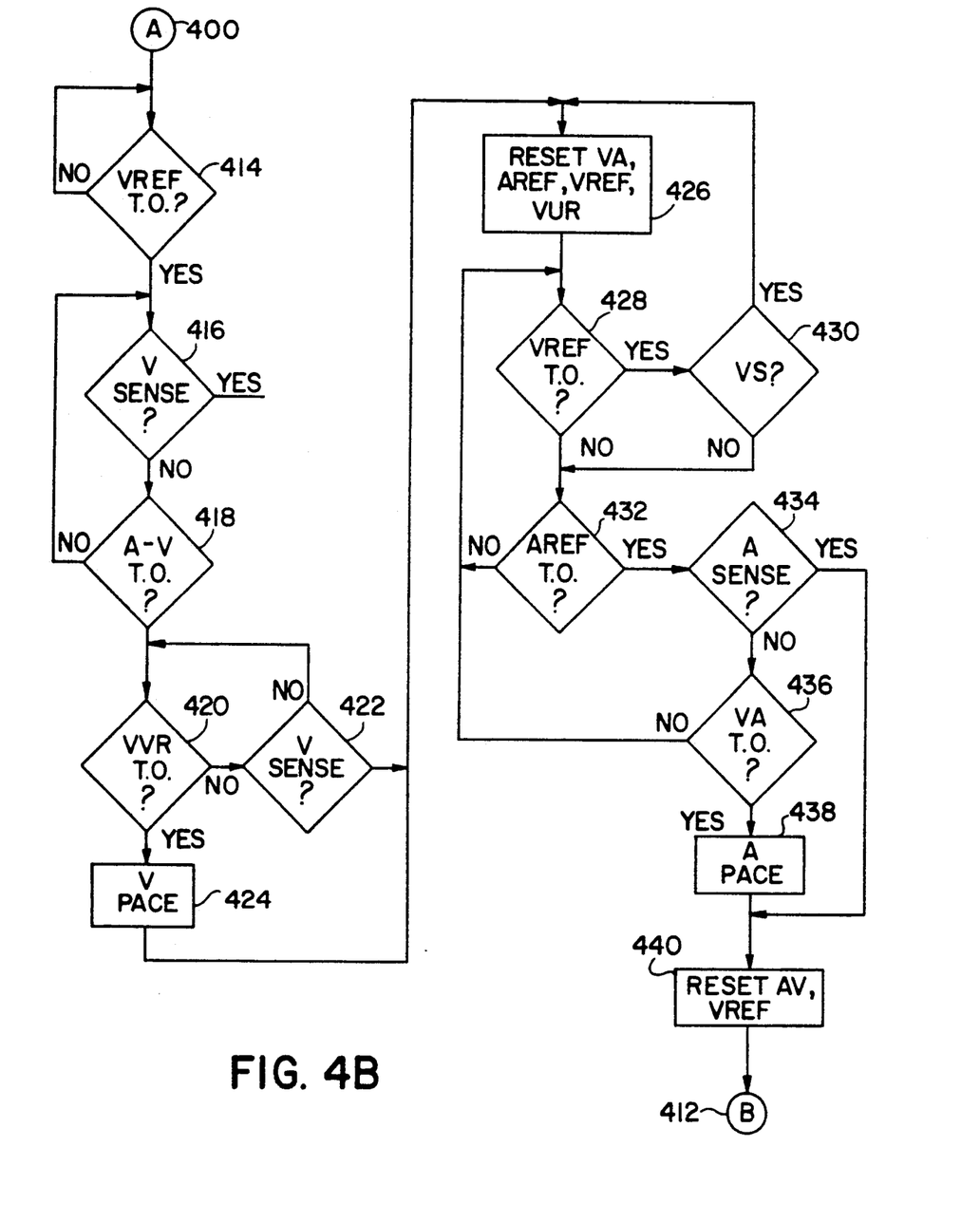

FIGS. 4A through 4D are functional flow charts illustrating the operation of several embodiments of the present invention. In the first embodiment, the burst stimulation function is provided in conjunction with a pacemaker programmed to operate in an atrial inhibited (AAI) pacing mode. In the second embodiment, the burst stimulation function is provided in conjunction with a pacemaker programmed to operate in a dual chamber (DDD) pacing mode. The basic operation of the device as an AAI pacemaker is illustrated in FIG. 4A. The basic operation of the device as a DDD pacemaker is illustrated in FIG. 4B.

Figure 4C:
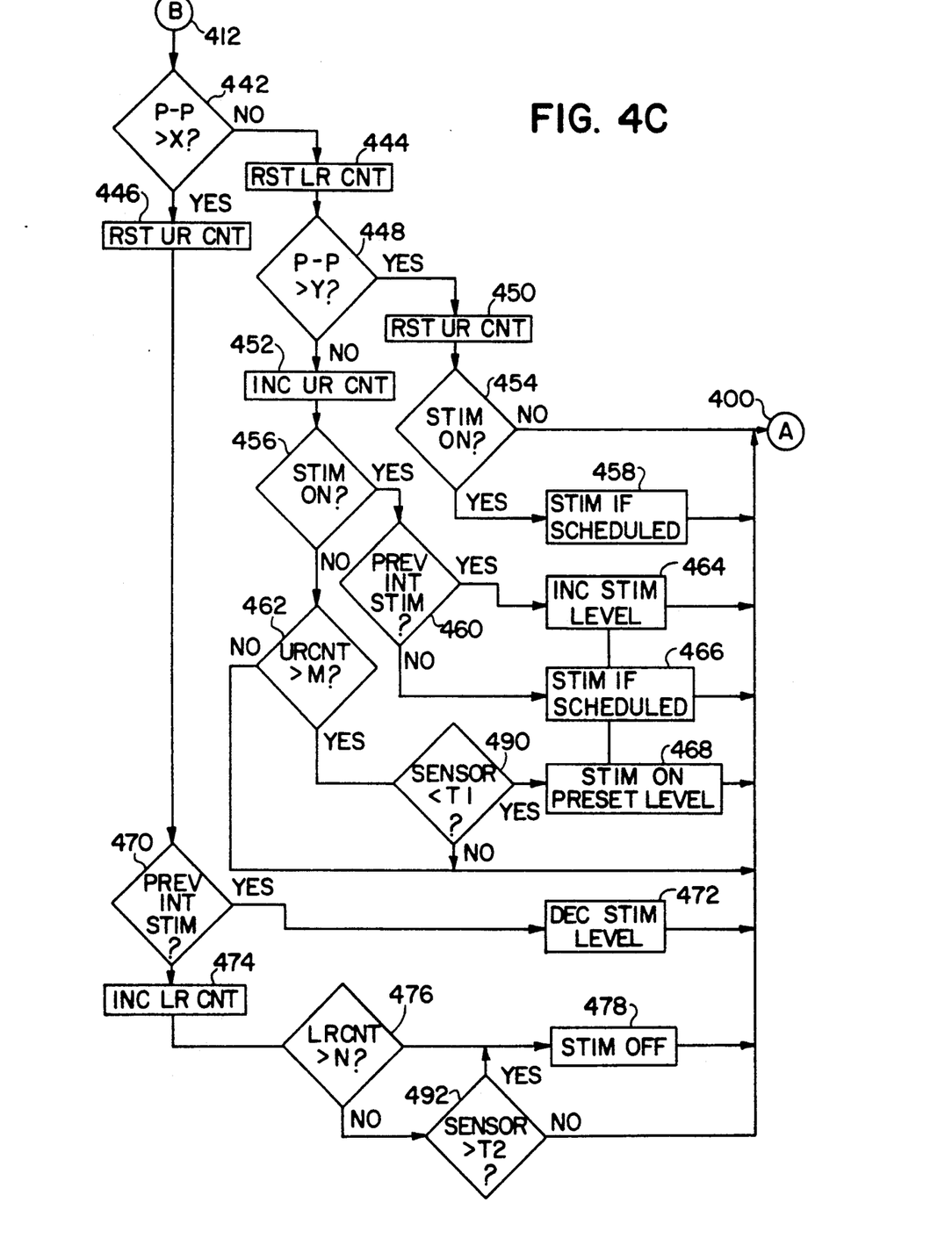
Figure 4D:
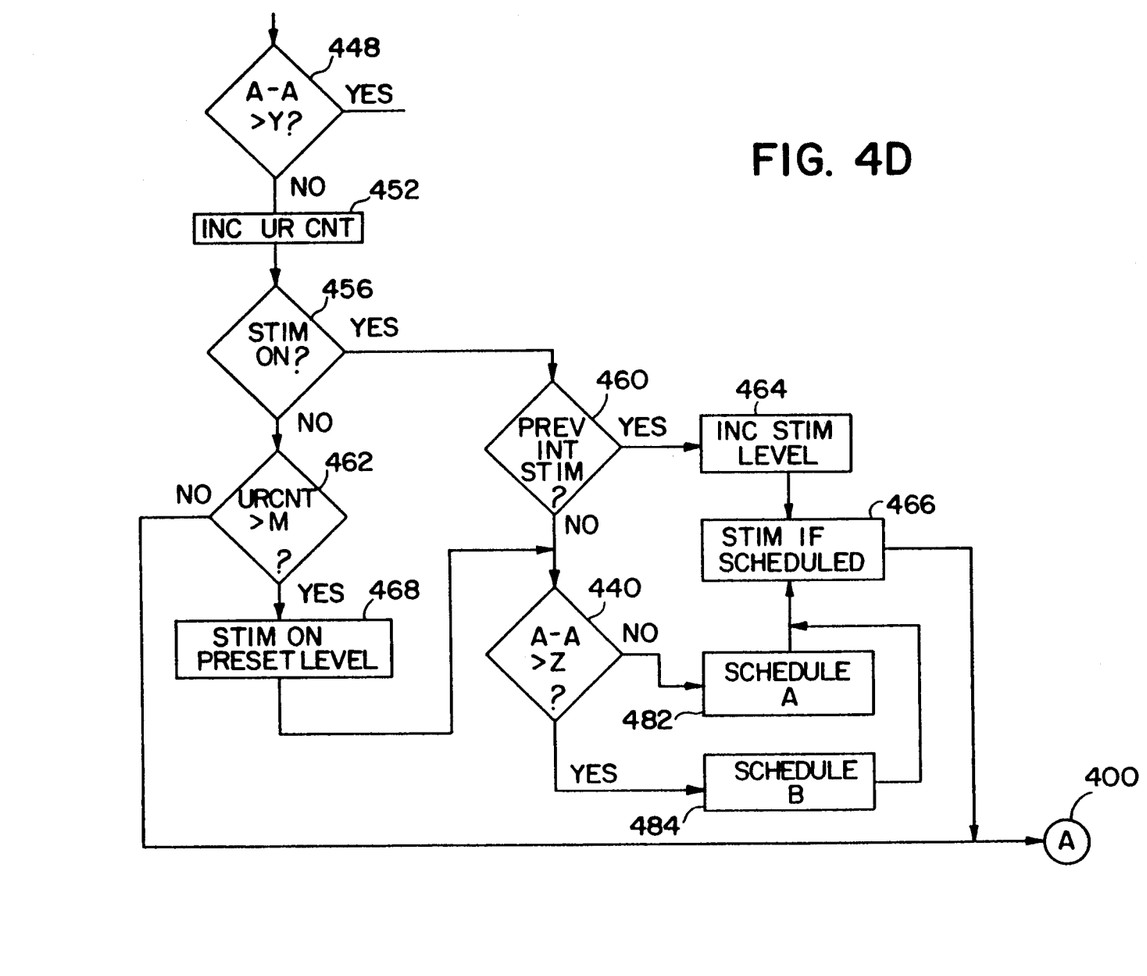

FIGS. 4C and 4D disclose alternative methods of implementing the burst stimulation function. In FIG. 4C, the burst stimulation function is provided with a fixed therapy schedule. In other words, after activation of the burst stimulation function, pulse bursts are delivered synchronized to each sensed atrial depolarization occurring at a rate above the intermediate rate.

An alternative embodiment is illustrated in FIG. 4D, in which the therapy schedule may be varied in response to variations in sensed atrial rhythm. In other words, if the intrinsic atrial rhythm is only slightly above the upper rate necessary to initiate burst pacing, pulse bursts will be delivered synchronized only to one out of every two or one out of every three P-waves occurring at a rate above the intermediate rate. In response to detection of an atrial rhythm substantially in excess of the upper rate necessary to initiate burst pacing, pulse bursts are delivered synchronized to each detected P-wave occurring at a rate above the intermediate rate. FIGS. 4A and 4B may each be combined with either of FIGS. 4C and 4D to provide individual embodiments of single and dual chamber pacemakers employing the present invention.

FIG. 4A illustrates the functional organization of the software controlling atrial pacing in the AAI mode. This portion of the software is entered at 400 in response to exiting the software in either FIG. 4C or 4D, related to the burst pacing function, very shortly after the delivery of an atrial pacing pulse or the sensing of a spontaneous atrial depolarization or "P wave".

Following delivery of an atrial pacing pulse or sensing of a P-wave, the atrial refractory and atrial escape intervals are reset. The atrial escape interval is an interval initiated in response to a sensed P-wave or the delivery of an atrial pacing pulse. If no P waves are sensed prior to expiration of the escape interval, an atrial pacing pulse is generated at the expiration of the atrial escape interval. The atrial refractory period is likewise initiated in response to sensing of a P wave or delivery of an atrial pacing pulse, and defines a period of time during which a subsequent P wave will be ineffective to restart the atrial escape interval.

After expiration of the refractory period at 402, the microprocessor 324 awaits an interrupt indicating either the occurrence of an atrial depolarization at 404 or the time out of the atrial escape interval at 408. In response to sensing of a P-wave, the atrial refractory period and atrial escape interval are reset at 406, and the portion of the software dedicated to controlling operation of the burst pacing function is entered at 412. In response to an interrupt indicating expiration of the atrial escape interval at 408, an atrial pacing pulse is delivered at 410 and the atrial escape interval and atrial refractory intervals are correspondingly reset at 406.

FIG. 4B illustrates the operation of a pacemaker embodying the present invention, programmed to operate in the DDD pacing mode. As in the case of FIG. 4A, the entry point for this portion of the software at 400 is the exit point for the software in FIGS. 3C and 3D related to control of the burst pacing function. The exit point of the software at 412 is the entry point to the software controlling the burst pacing function, illustrated in FIGS. 4C and 4D.

As a practical matter, the entry point for the software of FIG. 4B at 400 occurs in response to a sensed P-wave or the delivery of atrial pacing pulse. A ventricular refractory period and an A-V interval are initiated in response to either a sensed P-wave or delivery of an atrial pacing pulse. Upon expiration of the A-V interval, a ventricular pacing is delivered. If a ventricular depolarization or R-wave is sensed during the A-V interval, the A-V interval will be terminated and a subsequent V-A interval will be initiated. The ventricular refractory interval defines a period of time beginning with either an atrial pacing pulse or a sensed P-wave, during which a sensed R-wave will be ineffective to terminate timing of the A-V interval.

Following expiration of the ventricular refractory interval at 414, the microprocessor 324 (FIG. 3) awaits the occurrence of either an interrupt indicative of a sensed R-wave at 416 or indicative of A-V time out at 418. In the event that a ventricular contraction is sensed during the A-V interval, the V-A interval is initiated, along with an atrial refractory interval, a new ventricular refractory interval and the ventricular upper rate interval at 426. The V-A interval is initiated on ventricular pacing or sensing.

On expiration of the V-A interval, an atrial pacing pulse will be delivered unless an atrial or ventricular depolarization is sensed prior to expiration of the V-A interval, which will result in resetting of the A-V or V-A interval, respectively. As in the case of the atrial and ventricular refractory intervals discussed above, the atrial and refractory intervals following ventricular pace or sense define time periods during which an atrial or ventricular depolarizations, respectively, will be ineffective to reset the timing of the pacemaker. The ventricular upper rate interval, initiated on ventricular sensing or pacing defines a time period during which delivery of a ventricular pacing pulse is prohibited.

In the event that the A-V interval does time out, the microprocessor 324 checks to determine whether the ventricular upper rate interval initiated on the previous ventricular pacing pulse or sensed ventricular depolarization has expired at 420. If not, the microprocessor waits for an interrupt indicating either expiration of the ventricular upper rate interval or the occurrence of a sensed ventricular contraction. If a ventricular contraction is sensed, the V-A atrial refractory, ventricular refractory and ventricular upper rate intervals are reset at 426 as discussed above. If the ventricular upper rate interval times out prior to ventricular sensing, a ventricular pacing pulse is delivered at 424, followed by restarting of the V-A, atrial refractory, ventricular refractory and ventricular upper rate intervals at 426.

Following a ventricular pacing pulse or sensed ventricular depolarization, the microprocessor checks at 428 to determine whether the ventricular refractory period has expired. If so, it will respond to interrupts indicative of ventricular sensing at 430, and will reset the V-A, atrial refractory, ventricular refractory and ventricular upper rate intervals in response thereto. If the ventricular refractory period has not timed out, the microprocessor will not respond to sensed ventricular depolarizations in this fashion. The microprocessor similarly checks to determine whether the atrial refractory interval has timed out at 432. If so, microprocessor will be responsive to interrupts indicative of atrial depolarizations at 434, to reset the A-V and ventricular refractory intervals at 440.

In the absence of a sensed ventricular depolarization or sensed atrial depolarization prior to expiration of the V-A interval, the interrupt indicating time out of the V-A interval at 436 will trigger the microprocessor to deliver an atrial pacing pulse at 438 and to restart the A-V interval and the ventricular refractory period as discussed above at 440. As such, in both FIGS. 4A and 4B the entry point to the portion of the software controlling the burst pacing function is a sensed or paced event occurring in the atrium.

FIG. 4C illustrates the functional organization of software controlling the operation of a first embodiment of the invention. In response to delivery of an atrial pacing pulse or a sensed P-wave, this portion of the software is entered at 412. The most recent P—P interval is compared to the intermediate rate interval at 442. If the P—P interval is greater than the intermediate rate interval, an upper rate count is reset at 446. The upper rate count is a count equal to the number of successive P—P intervals less than the upper rate interval.

The microprocessor checks at 470 to determine whether burst stimulation was delivered synchronized to the atrial event (paced or sensed) that began the previous P—P interval. If so, the fact that the measured P—P interval exceeds the intermediate rate interval is used as an indication that the amplitude of the stimulus burst is excessive, and the stimulation amplitude is decremented at 472. Because the P—P interval reflects a rate below the intermediate rate, no stimulus burst is delivered.

In the event that the atrial event which initiated the previous P—P interval was accompanied by a stimulus burst, the intermediate rate count is incremented at 474, and the microprocessor checks to determine whether the lower rate count exceeds a predetermined number "N", typically one to three. If so, this indicates the occurrence of at least one P—P interval in which the atrial event initiating interval reflecting a spontaneous atrial rate below the intermediate rate. This reflects a return of the spontaneous atrial rate to an acceptable level, so that the burst stimulation function can be turned off at 478. If the intermediate rate count is less than or equal to N, the device optionally checks at 492 to determine whether the average value of the sensor output is greater than a threshold value T2. The value of T2 is greater than the threshold value T1 employed for initiation, discussed below. If so, burst stimulation is disabled at 478. Otherwise, simply returns to bradycardia pacing at 400.

In the event that the measured P—P interval at 442 is less than or equal to the intermediate rate interval, the intermediate rate count is reset at 444, and the measured P—P interval is compared to the upper rate interval at 448. In the event that the measured interval is not greater than the upper rate interval, the upper rate count is incremented at 452. The upper rate count is the number of sequential P—P intervals less than or equal to the upper rate interval.

The microprocessor checks at 456 to determine whether the burst stimulation function was previously activated. If not, the upper rate count is compared to a predetermined value "M" to determine whether the burst stimulation feature should be activated. If the upper rate count is equal to or less than M at 462, the device simply returns to bradycardia pacing mode at 400. If the upper rate count is greater than M, the device optionally checks at 490 to determine whether the average value of the sensor output is less than a threshold value T1. If so, the burst stimulation function is activated at 468, and a stimulation pulse is delivered at 466. If not, the device simply returns to bradycardia pacing mode at 400. If the sensor is not employed, the device would simply activate burst stimulation when the upper rate count exceeds M at 462. This portion of the operation of the device corresponds to the initial portion of FIG. 1A, showing the activation of the burst pacing function.

In the event that the sensed P—P interval is less than or equal to the upper rate interval, and the atrial event associated with the initiation of the preceding P—P interval was accompanied by the delivery of a stimulus burst at 460, the device interrupts this as indicative of an inadequate level of burst stimulation, due to the failure to reduce the atrial rate below the upper rate. Therefore, the stimulation level is incremented at 464, and stimulation is delivered at 466. If, on the other hand, the P-wave initiating the previous interval was not accompanied by burst stimulation, the device simply delivers a stimulation pulse at 466 at the previous amplitude setting. This portion of the operation of the device is again reflected in FIG. 1A, illustrating the incrementation of stimulus amplitude in response to a pulse burst ineffective to prolong the P—P interval.

In the event that the P—P interval is greater than the upper rate interval but less than the intermediate rate interval, the upper rate count is reset at 450, and the device checks to determine whether the burst stimulation function was previously activated at 464. If not, the device simply returns to bradycardia pacing at 400. If the stimulation function is activated, a synchronized stimulus burst is delivered at 458, followed by a return to bradycardia pacing at 400. This portion of the operation of the device corresponds to the latter half of the illustration in FIG. 1A.

FIG. 4D illustrates an alternative approach to controlling the burst stimulus function. Functional blocks 448, 452, 456, 462, 468, 460, 464 and 466 correspond to the same functional blocks illustrated in FIG. 4C. Only additional new functional blocks 480, 482 and 484 are added.

The purpose of the additional functional blocks is to allow for a variation in therapy schedule. As discussed above, in this embodiment of the device, in response to detection of atrial rate slightly above the upper rate, stimulus pulses are delivered synchronized to one out of every two or three P-waves occurring at a rate above the intermediate rate. However, in response to detection of a spontaneous atrial rhythm substantially in excess of the upper rate, indicated at 480 by the occurrence of an P—P interval less than a an extreme upper rate interval, a more aggressive therapy schedule is selected at 482 which typically would provide for the delivery of a synchronized stimulus burst following each atrial event occurring at a rate above the intermediate rate.

While the above illustrated embodiments employ the sensor only to assist in activation and deactivation of burst stimulation, it is believed within the scope of the invention to employ the sensor for regulation of the burst stimulus amplitude as well. In such case, the sensor output may be employed to increment or decrement the burst stimulus amplitude depending on the relation of the sensor output to the thresholds T1 and T2, or other thresholds, in a fashion analogous to the use of the atrial rate to so regulate the burst stimulation amplitudes. The ability of the sensor to regulate burst amplitudes may be alternative to the use of atrial rate or may be limited by it such that increments and decrements indicated based on atrial rate take priority over increments and decrements based on the sensor output. Similarly, while the sensor and the atrial rate are used as conjunctive criteria for burst stimulation activation and alternative criteria for burst stimulation termination, other relationships are believed to be within the scope of the present invention.

Further. while the above invention is disclosed as embodied in atrial and dual chamber pacemakers, it should be understood that the invention may also be usefully practiced in conjunction with an implantable pacemaker/cardioverter/defibrillator, or with other forms of cardiac pacemakers. Moreover, while the device is disclosed as having fixed threshold rates and intervals for activation and disabling of the burst stimulus function, the invention may also be practiced in the context of rate responsive pacemakers, in which the escape intervals are varied as a function of demand for cardiac output. In such embodiments, it is envisioned that the upper rate and intermediate rates may similarly be varied as a function of the output of the physiologic sensor, so that the burst stimulus function will not be activated unless the atrial rate reflects a substantial departure from the expected atrial rate, given the patient's present exercise level.

Similarly while the above invention is disclosed in the context of a microprocessor based architecture, the operation of the device is simple enough that it may also be implemented by means of a full custom digital integrated circuit based architecture, or even an architecture employing analog timing circuitry. Therefore, the above disclosure should be considered exemplary, rather than limiting with regard to the claims that follow.

I claim:

1. A method of electrical stimulation, comprising:
   placing an electrode in an appropriate location surrounding for stimulating the SA nodal fat pad of a human heart;
   defining a first heart rate;
   sensing the rate at which said human heart is beating;
   providing said stimulus pulses to said electrode, synchronized to depolarizations of a chamber of said human heart, during refractory periods following said depolarizations, in response to the rate at which said heart is beating exceeding said first heart rate;
   determining the effect of said stimulus pulses on the rate at which said human heart is beating; and
   adjusting the amplitude of said stimulus pulses as a function of the determined effect of said stimulus pulses.

2. A method of electrical stimulation, comprising the steps of:
   placing an electrode in an appropriate location for stimulating the SA nodal fat pad of a human heart;
   defining a first heart rate;
   sensing the rate at which said human heart is beating;
   providing said stimulus pulses to said electrode, synchronized to depolarizations of a chamber of said human heart, during refractory periods following said depolarizations, in response to the rate at which said heart is beating exceeding said first heart rate;
   defining a second heart rate below said first heart rate; and
   pacing said human heart when the rate at which said human heart is beating falls below said second heart rate.

3. A method according to claim 2 further comprising the step of defining a third heart rate above said second heart rate, and wherein said step of providing said stimulus pulses to said electrode is continued only while the rate of said human heart is above said third rate.

4. A method according to claim 2, further comprising the steps of;
   determining the effect of said stimulus pulses on the rate at which said human heart is beating; and
   adjusting the amplitude of said stimulus pulses as a function of the determined effect of said stimulus pulses.

5. A method according to claim 1 or claim 4 wherein said step of determining the effect of said stimulus pulses on the rate of said human heart comprises comparing the rate of said human heart following delivery of said stimulus pulses to a predetermined upper rate and wherein said adjusting step comprises incrementing the amplitude of said stimulus pulses responsive to the failure of said stimulus pulses to reduce the rate of said human heart below said upper rate.

6. A method according to claim 5 wherein said step of determining the effect of said stimulus pulses on the rate of said human heart comprises comparing the rate of said human heart following delivery of said stimulus pulses to an intermediate heart rate less than said upper rate and wherein said adjusting step comprises decrementing the amplitude of said stimulus pulses in response to delivery of said stimulus pulses resulting in a reduction in a rate of said human heart below said intermediate rate.

7. An electrical medical stimulator, comprising:
   electrode means for delivery of electrical stimulation to the fat pad associated with the SA node of a human heart;
   means for sensing depolarizations of a chamber of said human heart to determine the rate at which said human heart is beating;
   pulse generator means responsive to said sensing means for generating stimulus pulses and for providing said stimulus pulses to said electrode means during the refractory period of said chamber of said heart;
   means for defining a first heart rate;
   initiating means responsive to said sensing means for initiating the operation of said pulse generator means in response to the rate of said human heart exceeding said first heart rate;
   means responsive to said sensing means and to said pulse generator means for determining the effect of said stimulus pulses on the rate of said human heart; and
   means for adjusting the energy of said stimulus pulses as a function of the detected effected of said stimulus pulses.

8. A stimulator according to claim 7 wherein said determining means comprises means for comparing the rate of said human heart following delivery of said stimulus pulses to a predetermined upper rate, and wherein said adjusting means is responsive to the failure of delivered stimulus pulses to reduce the heart rate of said human heart below said upper rate and in response thereto increments the energy of said stimulus pulses.

9. A stimulator according to claim 8 further comprising means for defining an intermediate rate below said upper rate and wherein said determining means compares the rate of said human heart following delivery of said stimulus pulses to said intermediate heart rate and, in response to delivery of said stimulus pulses resulting in a reduction of the rate of said human heart below said intermediate rate decrements the energy of said stimulus pulses.

10. A stimulator according to claim 9 further comprising means for defining a pacing rate below said intermediate rate and means for pacing said human heart when the rate of said human heart fails below said pacing rate.

11. An electrical medial stimulator, comprising:
   electrode means for delivery of electrical stimulation to the fat pad associated with the SA node of a human heart;
   means for sensing depolarizations of a chamber of said human heart to determine the rate at which said human heart is beating;
   pulse generator means for generating stimulus pulses and for providing said stimulus pulses to said electrode means;
   means for defining a first heart rate;
   initiating means responsive to said sensing means for initiating the operation of said pulse generator means in response to the rate of said human heart exceeding said first heart rate;
   means for sensing a physiologic parameter other than heart rate and for providing an output signal indicative thereof; and
   means for defining a first sensor threshold; and wherein said initiating means further comprises means responsive to said output signal meeting said sensor threshold for initiating the operation of said pulse generator means.

12. A stimulator according to claim 11 further comprising
means for defining a second sensor threshold different from said first sensor threshold; and
deactivating means responsive to said output of said sensor means meeting said second sensor threshold for terminating the operation of said pulse generator means.

13. A stimulator according to claim 11, further comprising means responsive to said sensing means and to said pulse generator means for determining the effect of said stimulus pulses on the rate of said human heart and means for adjusting the energy of said stimulus pulses as a function of the detected effect of said stimulus pulses.

14. An electrical medical stimulator, comprising:
electrode means for delivery of electrical stimulation to the fat pad associated with the SA node of a human heart;
means for sensing depolarizations of a chamber of said human heart to determine the rate at which said human heart is beating;
pulse generator means responsive to said sensing means for generating stimulus pulses and for providing said stimulus pulses to said electrode means;
means for defining a first heart rate;
means for defining an acceptable range of heart rates;
initiating means responsive to said sensing means for enabling the operation of said pulse generator means in response to the rate of said human heart exceeding said first heart rate; and
means responsive to said sensing means and to said pulse generator means for determining the effect of said stimulus pulses on the rate of said human heart and means for adjusting the energy of said stimulus pulses, while said pulse generator is enabled, as a function of the determined effect of said stimulus pulses, to maintain said heart rate within said acceptable range of heart rates.

15. A stimulator according to claim 7 or claim 11 or claim 14 wherein said means for sensing the rate of said human heart comprises means for sensing atrial depolarizations of said human heart.

16. A stimulator according to claim 7 or claim 11 or claim 14 further comprising means for defining a second heart rate and means for pacing said human heart when said sensed heart rate falls below a second heart rate.

17. A stimulator according to claim 16 wherein said pacing means comprises means for pacing the atrium of said human heart.

18. A stimulator according to claim 17 further comprising means for defining a third heart rate above said second rate, wherein said pulse generator means is responsive to said means for defining said third heart rate, such that said pulse generator means provides said stimulus pulses to said electrode means only when the rate of said human heart is above said third heart rate.

19. A stimulator according to claim 7 or claim 11 or claim 14, further comprising means for defining a second rate below said first rate and further comprising deactivating means responsive to said sensing means for terminating the operation of said pulse generator means in response to the rate of said heart persistently falling below said second rate.

20. A stimulator according to claim 7 or claim 14, further comprising:
sensor means for sensing a physiologic parameter other than heart rate; and
means responsive to said sensor means for controlling the operation of said pulse generator means.

* * * * *